United States Patent [19]

Mueller

[11] 4,359,085
[45] Nov. 16, 1982

[54] INSTALLATION FOR SEVERAL SOUND AND/OR HEAT EMITTING MACHINES CAPABLE OF BEING INSTALLED IN A WORKROOM

[75] Inventor: Lothar Mueller, Darmstadt, Fed. Rep. of Germany

[73] Assignee: Siemens Aktiengesellschaft, Berlin & Munich, Fed. Rep. of Germany

[21] Appl. No.: 90,356

[22] Filed: Nov. 1, 1979

[30] Foreign Application Priority Data

Nov. 24, 1978 [DE] Fed. Rep. of Germany ... 7834992[U]

[51] Int. Cl.³ .............................................. F24H 3/00
[52] U.S. Cl. ...................................... 165/47; 165/135; 181/202; 181/224; 361/384; 62/DIG. 10; 312/209; 417/312; 433/104
[58] Field of Search ........................... 165/47, 51, 135; 181/200, 202, 204, 224, 225; 433/77, 91, 97, 98, 104; 361/379, 384, 390; 312/209; 417/312; 62/DIG. 10

[56] References Cited

U.S. PATENT DOCUMENTS

| | | | |
|---|---|---|---|
| 3,478,958 | 11/1969 | Hinck et al. | 181/200 |
| 3,553,840 | 1/1971 | Bordelon | 433/77 |
| 3,734,122 | 5/1973 | Cousins | 433/98 |
| 3,989,415 | 11/1976 | Van Hee et al. | 181/224 X |
| 4,146,112 | 3/1979 | Usry | 181/202 |
| 4,217,952 | 8/1980 | Kelly | 165/47 X |

Primary Examiner—Samuel Scott
Assistant Examiner—Margaret A. Focarino
Attorney, Agent, or Firm—Hill, Van Santen, Steadman, Chiara & Simpson

[57] ABSTRACT

In the exemplary embodiment, two machines are arranged in a common cabinet-like housing insulated toward the exterior from sound conducted through solids and airborne sound. For the purpose of fresh air supply to the machines, there are provided common fresh air channels connected via an inlet port with the exterior air. In order to discharge the exhaust air, separately arranged exhaust air chambers and/or exhaust air channels are provided which discharge into the open air via a common outlet port, disposed at a location remote from the inlet port. The fresh air channels and the exhaust air channels are so designed and arranged that the air is deflected many times during its flow through the housing. The installation particularly serves the purpose of housing dental vacuum generating and compressed air generating electric machines.

11 Claims, 3 Drawing Figures

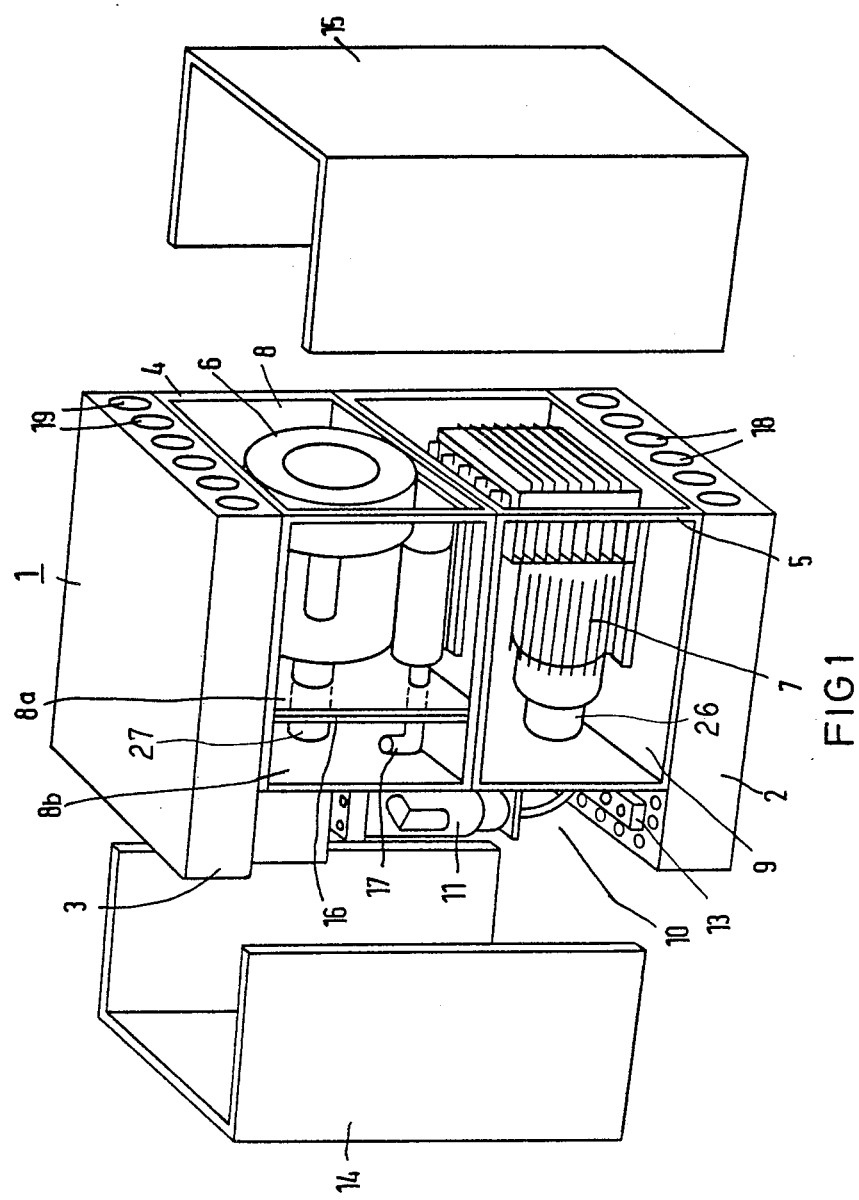

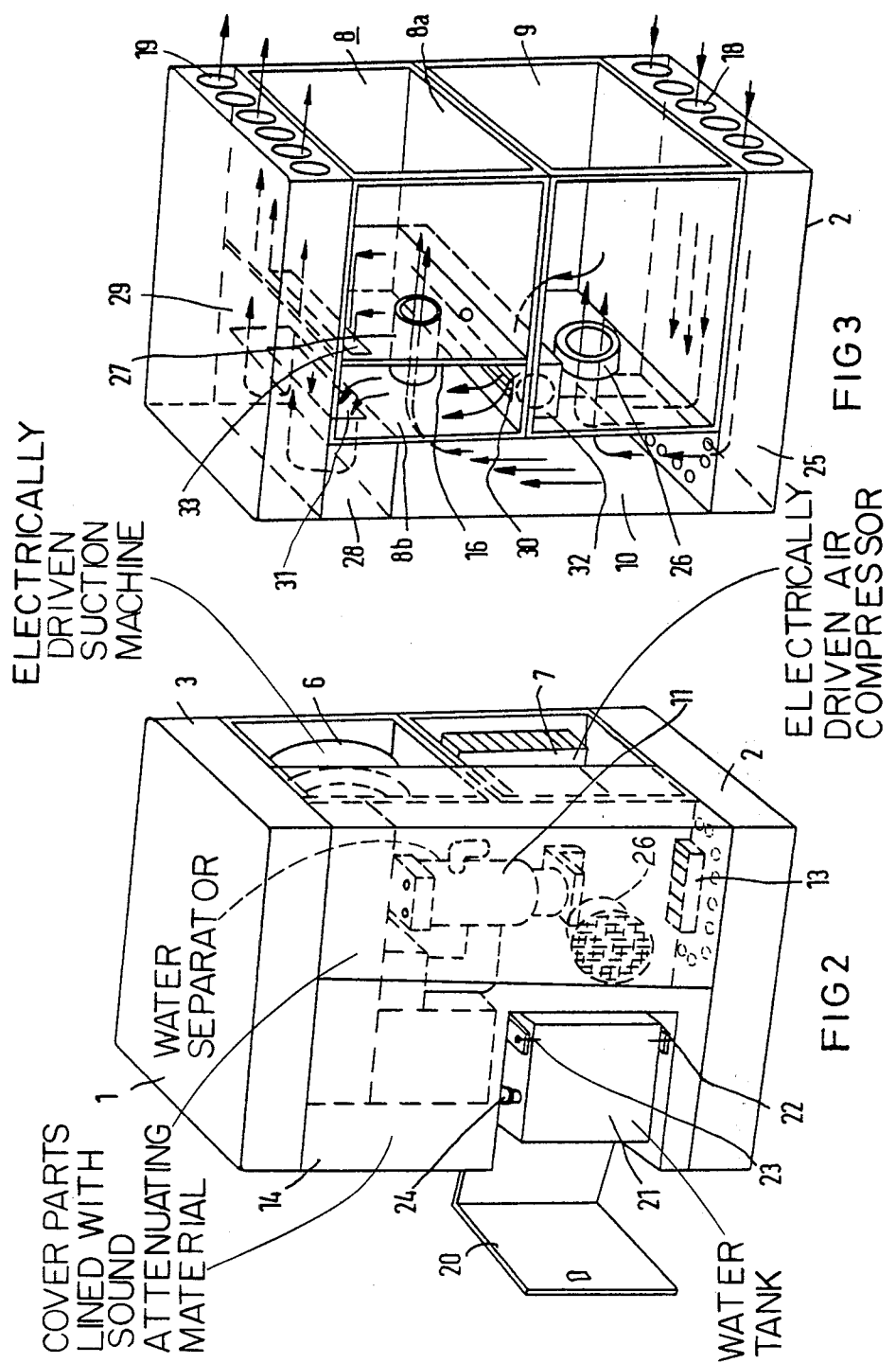

1

INSTALLATION FOR SEVERAL SOUND AND/OR HEAT EMITTING MACHINES CAPABLE OF BEING INSTALLED IN A WORKROOM

BACKGROUND OF THE INVENTION

The invention relates to an installation for several sound and/or heat emitting machines which can be installed in a workroom, in particular, vacuum and compressed air generating electric machines.

In workrooms in which work is carried out with sound and/or heat emitting machines; for example, with vacuum machines and compressors which are driven by electric motors, such as, for example, in saddlery or similar workshops, where vacuum machines for exhausting of adhesive vapors, on the one hand, and compressors for the operation of compressed air nailers, on the other hand, are utilized, or also in dental workrooms where such machines—even if for another purpose—are likewise utilized, the demand frequently exists to be able to install the machines in direct proximity to the work area. Due to the disturbing noises, such machines have hitherto been able to be installed only outside the workrooms; for example, in basement rooms, and this has in turn required a relatively costly laying in cables, in part, for example, in rented rooms; such installation frequently cannot even be carried out in the case of existing facilities.

SUMMARY OF THE INVENTION

The object of the present invention is to disclose an installation which permits the arrangement of several sound and/or heat emitting machines in a space-saving fashion as close as possible in the proximity of a working area without the occurrence of a disturbing noise development in the case of such an arrangement.

The problem posed is solved, in the case of an installation of the type initially cited, in accordance with the invention by virtue of the fact that the machines are arranged in a common cabinet-like housing, insulated toward the exterior against sound conducted through solids and airborne sound, that for fresh air supply to the machines, common fresh air channels are present which are connected with the exterior air via an inlet opening, and for discharging the exhaust air from the fresh air channels, separately arranged exhaust air chambers and/or exhaust air channels are present which lead into the open air via a common outlet orifice disposed at a location which is arranged removed from the inlet orifice, and that the fresh air channels and the exhaust air channels are designed and arranged such that the air, in its flow-through, is deflected therein many times.

With the proposed arrangement, an optimum noise attenuation of sound conduced through solids as well as of airborne sound is achieved and, at the same time, a good discharge of the heat due to energy losses is provided. Through the special air circulation with separate fresh air and exhaust, and the deflection of the air in the air circulation chambers and channels, the suction intake and air exhaust noises are so low that the machines can be arranged in direct proximity to the work area. The proposed arrangement also permits the arrangement of more than two machines in a space-saving fashion in this advantageous manner.

Advantageous embodiments and further developments of the invention are defined in the subclaims. An exemplary embodiment of the invention shall be explained in greater detail below on the basis of the accompanying sheets of drawings; and other objects, features and advantages will be apparent from this detailed disclosure and from the appended claims.

BRIEF DESCRIPTION OF THE DRAWINGS

FIG. 1 illustrates an installation of the inventive type with removed housing covers in a somewhat diagrammatic perspective view;

FIG. 2 illustrates the installation in another perspective view with the housing covering applied; and FIG. 3 illustrates the division of the housing and the air circulation in the housing of the installation in a diagrammatic perspective illustration.

DETAILED DESCRIPTION

FIG. 1 illustrates the inventive installation provided for application in dental practice. The installation essentially consists of a cabinet-like housing 1 with a base support 2 and a cover-side support 3. Between both supports 2, 3, there are disposed rectangular frames 4, 5, as carriers for an electrically driven vacuum (or suction) machine 6 on the one hand and an electric compressor 7. By means of the frames 4, 5, two chambers 8, 9, disposed on top of one another, are formed which, in their surface area, claim approximately two-thirds of the surface area of the housing 1. In the remaining, adjacently disposed, space 10, a separation device 11 for the agents (water and air) suctioned-off by the vacuum (or suction) machine 6, a water tank 21 (FIG. 2), as well as diverse central connecting terminals and connecting fittings 13 for the two machines 6, 7, are arranged. Reference numerals 14 and 15 designate two U-shaped covering parts lined with a sound-attenuating material which insulate the housing 1 toward the exterior from sound conducted through solids and airborne sound.

The upper of the two superposed chambers 8 and 9 is subdivided by a separation wall 16 into two chamber sections 8a and 8b. The exhaust air outlet 17 of the vacuum (or suction) machine 6 leads into the chamber section 8a. Reference numeral 18 designates a suction (or intake) opening, arranged in the support 2, by way of which the two machines 6 and 7 take in fresh air. The heated exhaust air is blown out via an outlet orifice arranged in the support 3 and arranged at a distance from the intake orifice 18.

As can be seen from FIG. 2, the facing (or lining) part 14 contains a hinged door 20 via which access to a water tank 21 is provided. The water tank 21 is swingable about a vertical axis 23 toward the exterior by means of an upright U-shaped frame 22, and contains a feed opening (or filling hole) 24 on its upper side.

FIG. 3 illustrates the space-division of the housing 1 and the air circulation path to or from the machines 6 and 7 which are not shown in this illustration. In the base support 2, a fresh air channel 25 is arranged, which is connected with the exterior air via the inlet port 18, which fresh air channel merges into the space 10 (see FIG. 1). The fresh air is supplied to both machines 6, 7, via channels 26, 27, FIG. 3.

The exhaust air system is separated from the fresh air channel system 25, 10 and 26, 27, and is formed by the chambers 8a and 9, in which the machines 6, 7 are installed, on the one hand, and by the chambers 8b as well as additional exhaust air channels 28, 29, which are connected with the outlet port 19, on the other hand. The exhaust air channel 29 with the outlet port 19, since it is disposed in the cover-side support 3, is arranged at a marked distance from the fresh air channel 25, so that no heated exhaust air is taken in via the fresh air channel.

The exhaust air chamber 9 is connected via an opening 30 with the chamber section 8b which, in turn, leads into the exhaust air channel 28 via an additional opening 31. In order to additionally support the air flow, there is arranged, beneath the opening 30, a blower installation 32 which provides for an acceleration of the exhaust air. The arrangement of a blower installation is particularly advisable when the exhaust air of the vaccum (or suction) machine 6 is not, or cannot—as in the present instance—be blown into the chamber 8b, and thus (on account of the stronger air current), as a rule, a sufficiently good exhaust of the heated exhaust air is already achieved. Also the exhaust air from the chamber 8a leads into the chamber section 8b via an additional opening 33. The ports 31 and 33 are disposed at approximately the same height.

As is apparent from the air flow direction illustrated by the arrows, as a consequence of the described arrangement of the channels and chambers, the fresh air as well as the exhaust air is deflected through channels many times. The fresh air chambers and channels as well as the exhaust air chambers and channels are all lined with sound-attenuating material, as a consequence of which, and particularly due to the multiple deflection of the air flow path, no disturbing noises occur on the intake (or suction) side as well as on the outlet (or discharge) side. In order to guarantee an optimum insulation, the housing chambers 8 and 9 can be expediently covered, on the open sides (see FIG. 1), with additional lining (or covering) metal plates provided with sound attenuating material, over which the U-shaped housing plate 15 is then arranged. The frames 4, 5, can be formed from profile sections as well as from bent (or curved) metal plates, whereby, however, openings then remain free on two opposite sides for loading and unloading the machine, which openings, after assembly of the machine, are covered by additional lining (or covering) metal plates before the U-shaped lining (or covering) metal plate 15 is slipped on.

The inventive installation contains, in a compact external form, all those machines and devices which are necessary for many purposes, particularly for the operation of dental handpieces, in order to be able to offer the required fluid agents (water, compressed air, and intake (or suction) air water-air-mixture). Through the arrangement of the water tank 21, which serves the purpose of supplying diverse handpieces with cooling agents and which is charged with compressed air by the compressor 7, the installation is independent of the conventional water supply system.

It will be apparent that many modifications and variations may be effected without departing from the scope of the novel concepts and teachings of the present invention.

I claim as my invention:

1. An installation for several sound and/or heat emitting machines to be installed in a workroom, in particular, vacuum generating and compressed air generating electric machines, said installation comprising a common cabinet-like housing (1) for the machines, insulated toward the exterior against sound conducted through solids and airborne sound, said housing having fresh air supply means for supplying fresh air to the machines comprising a fresh air inlet (18) and fresh air channels (25, 10, 26, 27), connected via said inlet (18) with exterior air, and said housing having air exhaust means for discharging air from the vicinity of the machines and comprising exhaust air confining means (8a, 9, 8b, 28 and 29) and a common outlet (19) disposed at a location which is arranged removed from the inlet (18), the fresh air channels and exhaust air confining means being constructed and arranged so that the air is deflected many times in the course of its flow from the inlet to the outlet, the housing having mutually separate housing chambers (8, 9) for receiving the machines, which at the same time form exhaust air chambers into which the heated exhaust air of the machines flows, said exhaust air confining means comprising a common exhaust air channel (28, 29) and the exhaust air chambers (8, 9), said exhaust air chambers (8, 9) each supplying exhaust air to the common exhaust air channel (28, 29).

2. An installation according to claim 1, with the housing having therein at least one electrically driven suction machine (6) for dental purposes and an electrically driven air compressor (7) for dental purposes.

3. An installation according to claim 2, with the housing having therein a separation installation (11) for the agent suctioned-off by the suction machine (6).

4. An installation for several sound and/or heat emitting machines to be installed in a workroom, in particular, vacuum generating and compressed air generating electric machines, said installation comprising a common cabinet-like housing (1) for the machines, insulated toward the exterior against sound conducted through solids and airborne sound, said housing having fresh air supply means for supplying fresh air to the machines comprising a fresh air inlet (18) and fresh air channels (25, 10, 26, 27), connected via said inlet (18) with exterior air, and said housing having air exhaust means for discharging air from the vicinity of the machines and comprising exhaust air confining means (8a, 9, 8b, 28 and 29) and a common outlet (19) disposed at a location which is arranged removed from the inlet (18), the fresh air channels and exhaust air confining means being constructed and arranged so that the air is deflected many times in the course of its flow from the inlet to the outlet, the housing having superposed housing chambers (8, 9), and respective vacuum generating and compressed air generating electric machines (6, 7) in the respective housing chambers (8, 9), the housing chambers (8, 9) being interconnected via an opening (30), and the exhaust air confining means comprising an exhaust air channel (28, 29) communicating with the uppermost chamber (8).

5. An installation according to claim 4, with said air exhaust means further comprising a blower installation (32) for supporting the air circulation arranged at the opening (30) between the superimposed housing chambers (8, 9).

6. An installation for several sound and/or heat emitting machines to be installed in a workroom, in particular, vacuum generating and compressed air generating electric machines, said installation comprising a common cabinet-like housing (1) for the machines, insulated toward the exterior against sound conducted through solids and airborne sound, said housing having fresh air supply means for supplying fresh air to the machines comprising a fresh air inlet (18) and fresh air channels (25, 10, 26, 27), connected via said inlet (18) with exterior air, and said housing having air exhaust means for discharging air from the vicinity of the machines and comprising exhaust air confining means (8a, 9, 8b, 28 and 29) and a common outlet (19) disposed at a location which is arranged removed from the inlet (18), the fresh air channels and exhaust air confining means being constructed and arranged so that the air is deflected many times in the course of its flow from the inlet to the outlet, the housing having superposed housing chambers (8, 9), and respective vacuum generating and compressed air generating electric machines (6, 7) in the respective housing chambers (8, 9), the upper (8) of the two superposed chambers (8, 9) being subdivided by a thermally insulating separation wall (16) into a first section (8a) housing one of the machines (6), and into a second section (8b), connected via an opening (30) with the chamber (9) disposed therebelow, and both sections (8a, 8b), via openings (31, 33) disposed in the upper region thereof, being connected with one another, on the one hand, and with the exhaust air confining means (28, 29), on the other hand.

7. An installation according to claim 6, with the exhaust air confining means comprising generally horizontally disposed common exhaust air channel (29) leading to the outlet (19), the second section (8b) being a relatively narrow, uprightly arranged cuboid in relation to which the common exhaust air channel (29) is arranged at a right angle.

8. An installation for several sound and/or heat emitting machines to be installed in a workroom, in particular, vacuum generating and compressed air generating electric machines, said installation comprising a common cabinet-like housing (1) for the machines, insulated toward the exterior against sound conducted through solids and airborne sound, said housing having fresh air supply means for supplying fresh air to the machines comprising a fresh air inlet (18) and fresh air channels (25, 10, 26, 27), connected via said inlet (18) with exterior air, and said housing having air exhaust means for discharging air from the vicinity of the machines and comprising exhaust air confining means (8a, 9, 8b, 28 and 29) and a common outlet (19) disposed at a location which is arranged removed from the inlet (18), the fresh air channels and exhaust air confining means being constructed and arranged so that the air is deflected many times in the course of its flow from the inlet to the outlet, said fresh air channels including a common fresh air channel (25) arranged at the lower side of the housing (1), and the exhaust air confining means comprising an exhaust air channel (29) arranged at the upper side of the housing (1), the housing having housing chambers (8, 9), respective machines (6, 7) in the respective chambers (8, 9), said fresh air channels further comprising an additional common fresh air channel (10) for receiving incoming fresh air from the common fresh air channel (25) at the lower side of the housing (1), said additional common fresh air channel (10) being laterally next to said housing chambers (8, 9), and said fresh air channels further comprising separate intake channels (26, 27) leading from said additional common fresh air channel (10) to the respective housing chambers (8, 9) for supplying fresh air to said machines (6, 7) therein.

9. An installation according to claim 8, with the machines being electric machines, and the additional common fresh air channel (10) having therein connection means comprising connection terminals (13) necessary for the operation of the electric machines (6, 7).

10. An installation according to claim 9, with the additional common fresh air channel (10) having therein a water separator (11) and a water tank (21).

11. An installation according to claim 10, characterized in that a covering part (14) is provided enclosing the additional common fresh air channel (10), and having a hinged door (20) for providing access to the water tank (21).

* * * * *